US010886030B2

(12) United States Patent
Green et al.

(10) Patent No.: US 10,886,030 B2
(45) Date of Patent: Jan. 5, 2021

(54) PRESENTING CONTEXTUALLY RELEVANT PATIENT DATA IN RELATION TO OTHER PATIENTS TO A MEDICAL PROFESSIONAL

(71) Applicant: International Business Machines Corporation, Armonk, NY (US)

(72) Inventors: Jacob Green, Somerville, MA (US); Sarah Miller, Cambridge, MA (US); Jeffrey L. Sokolov, Lexington, MA (US); Paul C. Tang, Los Altos, CA (US)

(73) Assignee: International Business Machines Corporation, Armonk, NY (US)

( * ) Notice: Subject to any disclaimer, the term of this patent is extended or adjusted under 35 U.S.C. 154(b) by 448 days.

(21) Appl. No.: 15/857,120

(22) Filed: Dec. 28, 2017

(65) Prior Publication Data

US 2019/0206572 A1 Jul. 4, 2019

(51) Int. Cl.
G06F 3/00 (2006.01)
G16H 50/70 (2018.01)
G16H 70/20 (2018.01)
G16H 10/60 (2018.01)
G16H 50/20 (2018.01)
G06N 5/02 (2006.01)
G16B 40/00 (2019.01)

(52) U.S. Cl.
CPC ........... *G16H 50/70* (2018.01); *G06N 5/022* (2013.01); *G16B 40/00* (2019.02); *G16H 10/60* (2018.01); *G16H 50/20* (2018.01); *G16H 70/20* (2018.01)

(58) Field of Classification Search
CPC ............................................. G06F 16/24556
See application file for complete search history.

(56) References Cited

U.S. PATENT DOCUMENTS 7,433,827 B2 10/2008 Rosenfeld et al.
2005/0159987 A1 7/2005 Rosenfeld et al.
(Continued)

OTHER PUBLICATIONS

"The Era of Cognitive Systems: An inside look at IBM Watson and how it works", IBM Corporation, IBM Software Group, Whitepaper, IBM Watson Solutions, Sep. 2012, 19 pages.
(Continued)

*Primary Examiner* — Di Xiao
(74) *Attorney, Agent, or Firm* — Francis Lammes; Stephen J. Walder, Jr.; William J. Stock

(57) ABSTRACT

A mechanism is provided for presenting contextually relevant patient data in relation to other patients in a graphical user interface. Using a medical condition associated with a patient and a current treatment being followed by the patient, a cohort of similar patients with the same medical condition are identified. For each of the patients in the cohort, a set of next treatments are identified for those patients that stopped the current treatment and followed a next treatment. For each next treatment followed by a patent in the cohort of similar patients, a determination is made as to whether the next treatment controlled or failed to control the same medical condition for the patient. Then a presentation is provided indicating the set of next treatments, a number of patients following each next treatment, whether each treatment controlled or failed to control the same medical condition, and a statistical significance.

9 Claims, 4 Drawing Sheets

(56) References Cited

U.S. PATENT DOCUMENTS

| | | | |
|---|---|---|---|
| 2006/0122869 A9 | 6/2006 | Rosenfeld et al. | |
| 2012/0232930 A1* | 9/2012 | Schmidt | A61B 6/5217 705/3 |
| 2013/0226617 A1 | 8/2013 | Mok et al. | |
| 2015/0213194 A1* | 7/2015 | Wolf | G06K 9/00442 705/3 |
| 2016/0224760 A1* | 8/2016 | Petak | G16H 50/20 |
| 2017/0372029 A1* | 12/2017 | Saliman | G16H 10/60 |

OTHER PUBLICATIONS

Alemzadeh, Homa et al., "An NLP-based Cognitive System for Disease Status Identification in Electronic Health Records", IEEE, 2017 IEEE EMBS International Conference on Biomedical & Health Informatics (BHI), Feb. 16-19, 2017, 4 pages.

Deleger, Louise et al., "Building Gold Standard Corpora for Medical Natural Language Processing Tasks", American Medical Informatics Association, AMIA Annual Symposium Proceedings, vol. 2012, Nov. 3, 2012, pp. 144-153.

Demner-Fushman, Dina et al., "What can Natural Language Processing do for Clinical Decision Support?", National Institutes of Health, Author Manuscript, J Biomed Inform., vol. 42, No. 5, Oct. 2009, pp. 760-772.

* cited by examiner

PRESENTING CONTEXTUALLY RELEVANT PATIENT DATA IN RELATION TO OTHER PATIENTS TO A MEDICAL PROFESSIONAL

BACKGROUND

The present application relates generally to an improved data processing apparatus and method and more specifically to mechanisms for presenting contextually relevant patient data in relation to other patients to a medical professional.

An electronic health record (EHR) or electronic medical record (EMR) is the systematized collection of patient and population electronically-stored health information in a digital format. These records can be shared across different health care settings. Records are shared through network-connected, enterprise-wide information systems or other information networks and exchanges. EMRs may include a range of data, including demographics, medical history, medication and allergies, immunization status, laboratory test results, radiology images, vital signs, personal statistics like age and weight, and billing information.

EMR systems are designed to store data accurately and to capture the state of a patient across time. It eliminates the need to track down a patient's previous paper medical records and assists in ensuring data is accurate and legible. It can reduce risk of data replication as there is only one modifiable file, which means the file is more likely up to date, and decreases risk of lost paperwork. Due to the digital information being searchable and in a single file, EMRs are more effective when extracting medical data for the examination of possible trends and long term changes in a patient. Population-based studies of medical records may also be facilitated by the widespread adoption of EMRs.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method, in a data processing system, is provided for presenting contextually relevant patient data in relation to other patients to a medical professional in a graphical user interface. The illustrative embodiment analyzes electronic medical records (EMRs) of a patient to identify a medical condition associated with the patient. The illustrative embodiment identifies a set of treatments from a corpus of medical treatment guidelines for the patient's medical condition. The illustrative embodiment identifies a current treatment that the patient is following. The illustrative embodiment identifies a cohort of similar patients with the same medical condition as the patient's medical condition that have followed the current treatment. For those patients in the cohort of other patients that stopped the current treatment and followed a next treatment, the illustrative embodiment identifies a set of next treatments from the set of treatments that each patient of the cohort of similar patients followed. For each next treatment followed by a patient in the cohort of similar patients, the illustrative embodiment determines whether the treatment controlled or failed to control the same medical condition for the patient. The illustrative embodiment then presents, in a graphical user interface, the set of next treatments the cohort of similar patients were prescribed, a number of patients in the cohort of similar patients following each treatment in the set of next treatments, an indication as to whether each treatment in the set of next treatments controlled or failed to control the same medical condition for the cohort of similar patients, and a statistical significance comparing a number controlled of the cohort of similar patients in each next treatment to patients in the cohort of similar patients staying on the current treatment.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE SEVERAL VIEWS OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
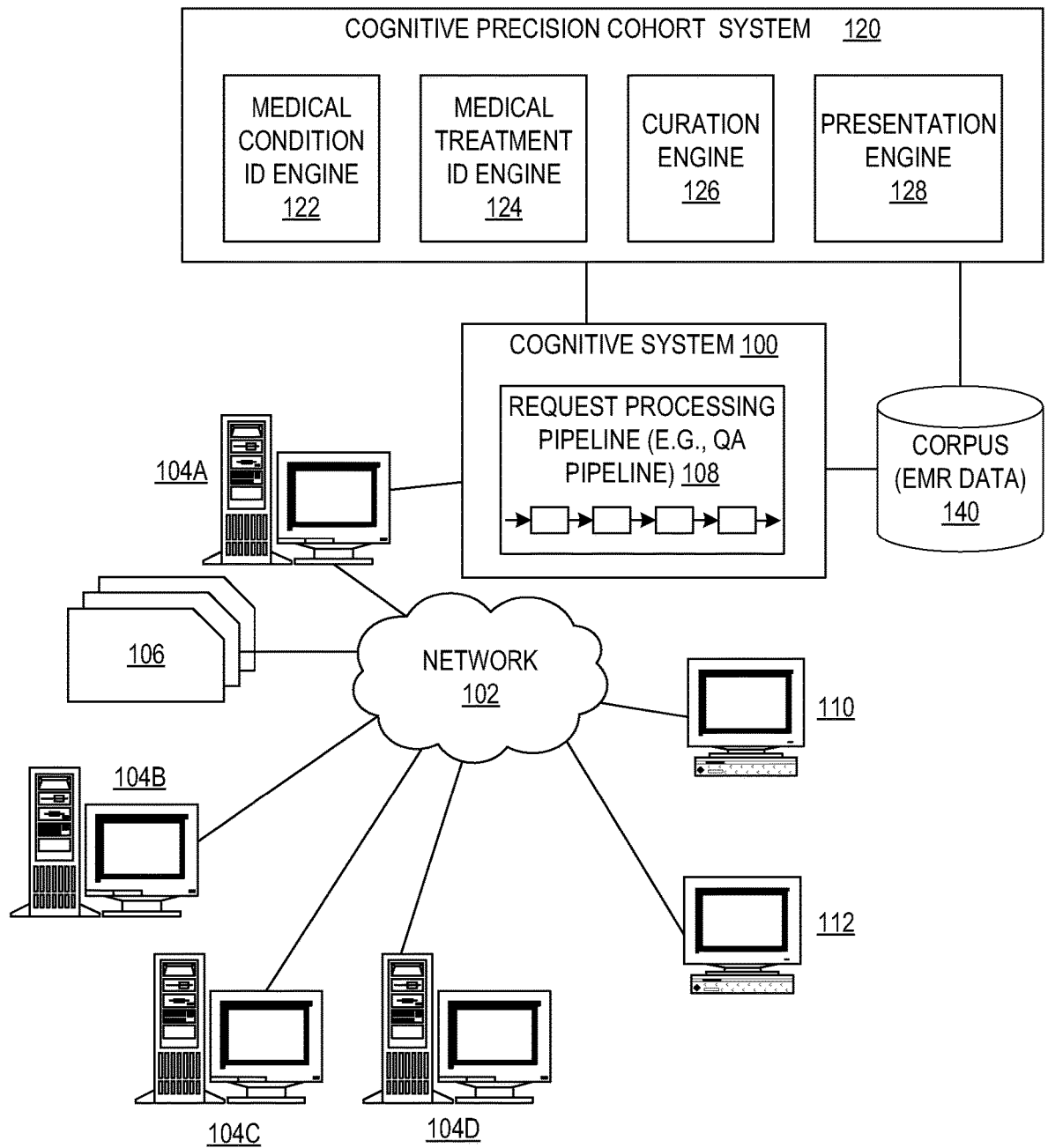
FIG. 1 depicts a schematic diagram of one illustrative embodiment of a cognitive system in a computer network.

The illustrative embodiments provide mechanisms for presenting contextually relevant patient data in relation to other patients to a medical professional in a graphical user interface. The cognitive precision cohort system generates a graphical user interface (GUI) that is configured to present the most relevant information for showing treatment outcomes for similar patients based on a context of the patient being treated. The GUI represents an entire patient population or a selected subset, hereinafter referred to as a patient cohort. The cognitive precision cohort system provides a historical data representation in the GUI of a cohort of similar patients that start with the treatment that the patient is currently on and who do not have their condition under control. For example, George, our patient is taking an Angiotensin II receptor blocker (ARB) to control his blood pressure and he does not have his blood pressure under control and all patients like George are taking an ARB and do not have their blood pressure controlled. The cognitive precision cohort system follows each next treatment path for a medical condition for the cohort of patients. An example of a treatment path is patients in the cohort who were next prescribed a diuretic to control their blood pressure. The cognitive precision cohort system also provides visual and numerical representation of information about the number of patients in the cohort following that treatment pathway, how many of those patients have their medical condition under control as well as those patients that do not have their medical condition under control. For each treatment pathway, the cohort of patients on that treatment and their outcomes are compared with patients in that cohort staying on the same treatment. For example, the cohort prescribed the diuretic might have 80% of patients with controlled blood pressure while the patients continuing on the ARB might have 40% of patients with their blood pressure controlled. The best to worst controlled next treatment pathways are ordered top to bottom. For each treatment pathway, the new treatment pathway is compared with continuing on the current pathway using a test of statistical significance and a visual representation is used to distinguish pathways that result in significantly different pathways than continuing on the same treatment path. For example, if the diuretic resulted in the highest percent of patients in the cohort with their blood pressure under control and that percent controlled was significantly different and better than continuing on the ARB, then the pathway would be a different color than the current pathway.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a," "at least one of," and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

Figure 2:
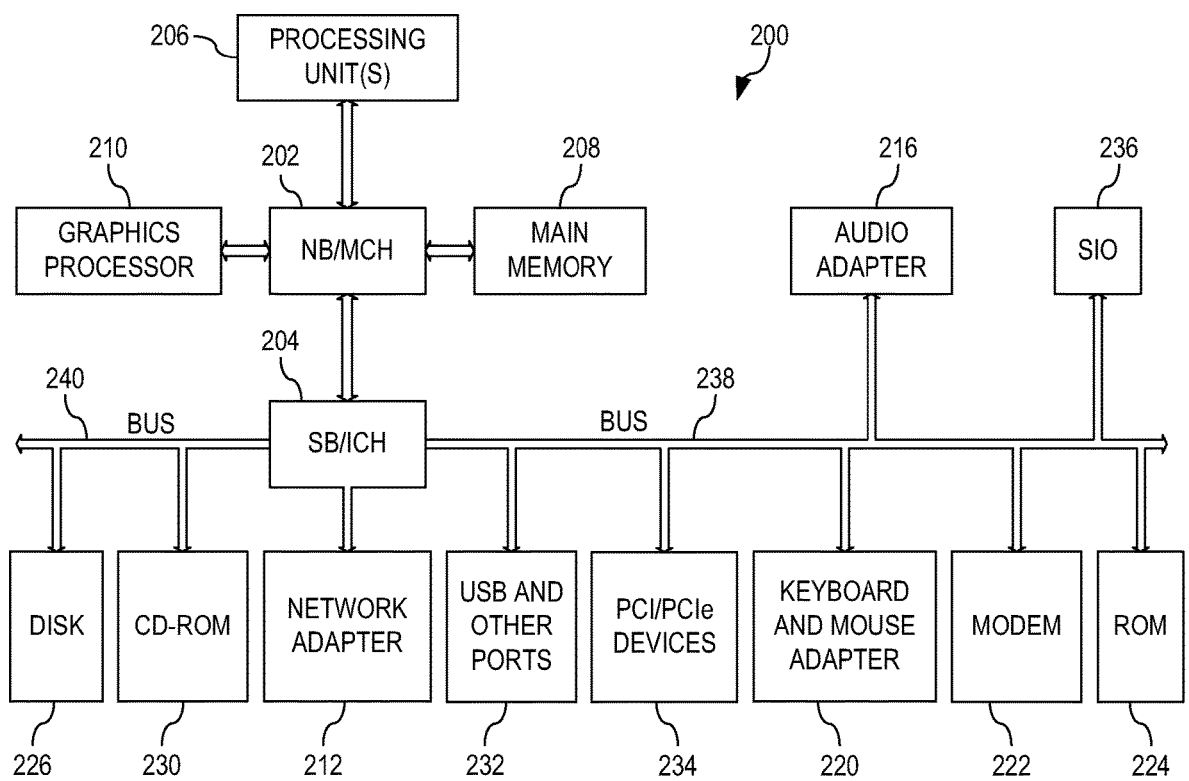
FIG. 2 is a block diagram of an example data processing system in which aspects of the illustrative embodiments are implemented.
Figure 3:
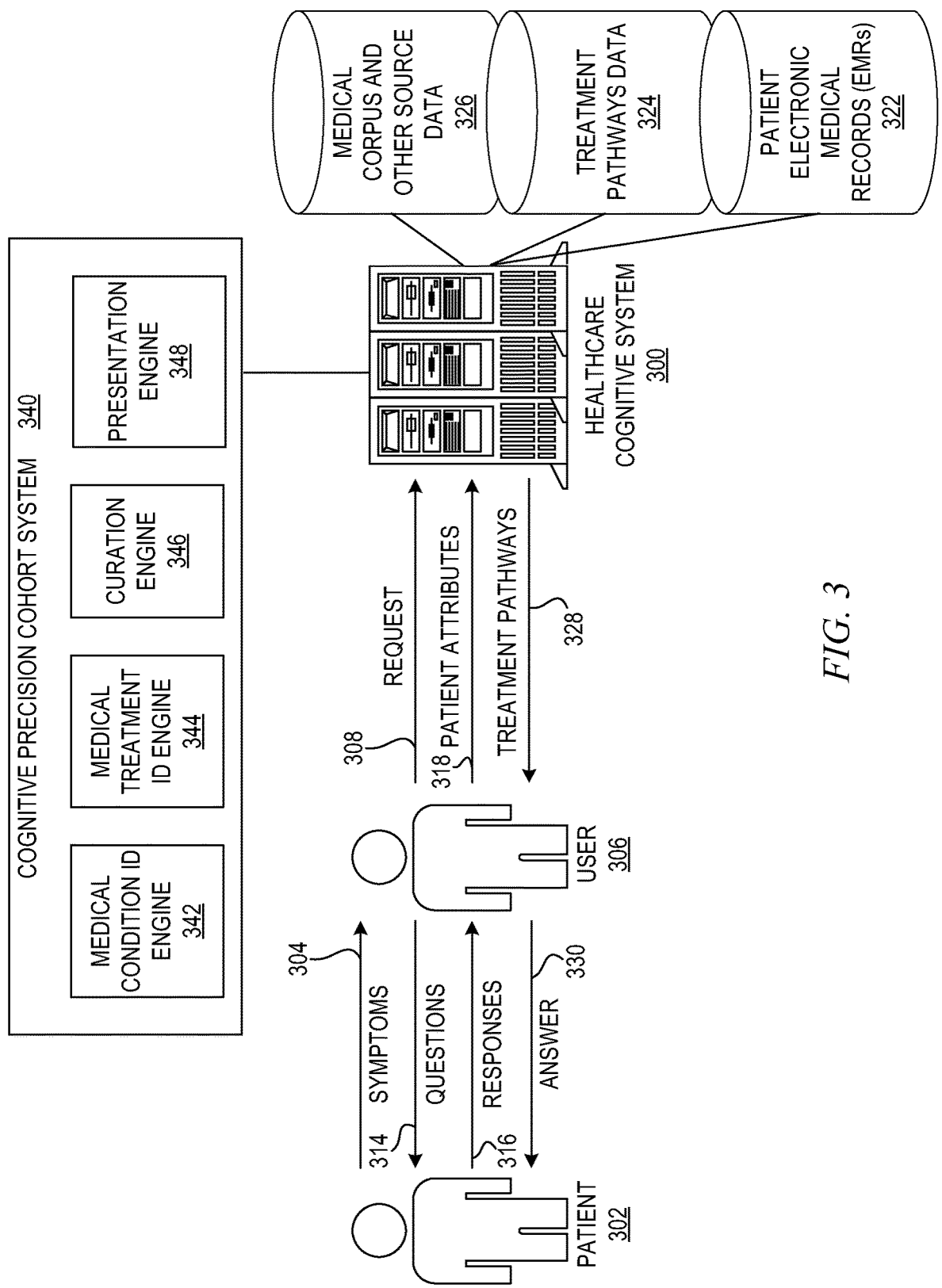
FIG. 3 is an example diagram illustrating an interaction of elements of a cognitive system in accordance with one illustrative embodiment.

As noted above, the present invention provides mechanisms for presenting contextually relevant patient data in relation to other patients to a medical professional in a graphical user interface. Thus, the illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

FIGS. 1-3 are directed to describing an example cognitive system for presenting contextually relevant patient data in relation to other patients to a medical professional in a graphical user interface that which implements a request processing pipeline, request processing methodology, and request processing computer program product with which the mechanisms of the illustrative embodiments are implemented. These requests may be provided as structure request messages, unstructured request messages or any other suitable format for requesting an operation to be performed by the cognitive system. As described in more detail hereafter, the particular application that is implemented in the cognitive system of the present invention is an application for presenting contextually relevant patient data in relation to other patients to a medical professional in a graphical user interface.

It should be appreciated that the cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests, depending on the desired implementation. For example, in some cases, a first request processing pipeline may be trained to operate on input requests directed to a providing a historical data representation in the GUI of patients that follow each treatment path for a medical condition. In other cases, for example, the request processing pipelines may be configured to provide different types of cognitive functions or support different types of applications, such as one request processing pipeline being used for identifying how many patients with a particular medical condition have their medical condition under control as well as patients with the same particular medical condition that do not have their medical condition under control.

Moreover, each request processing pipeline may have its own associated corpus or corpora that they ingest and operate on, e.g., one corpus for medical treatment guideline documents and another corpus for electronic medical record documents in the above examples. In some cases, the request processing pipelines may each operate on the same domain of requests but may have different configurations, e.g., different annotators or differently trained annotators, such that different analysis and potential responses are generated. The cognitive system may provide additional logic for routing requests to the appropriate request processing pipeline, such as based on a determined domain of the input request, combining and evaluating final results generated by the processing performed by multiple request processing pipelines, and other control and interaction logic that facilitates the utilization of multiple request processing pipelines.

It should be appreciated that while the present invention will be described in the context of the cognitive system implementing one or more request processing pipelines that operate on a request, the illustrative embodiments are not limited to such. Rather, the mechanisms of the illustrative embodiments may operate on requests that are posed as "questions" or formatted as requests for the cognitive system to perform cognitive operations on a specified set of input data using the associated corpus or corpora and the specific configuration information used to configure the cognitive system.

As will be discussed in greater detail hereafter, the illustrative embodiments may be integrated in, augment, and extend the functionality of the request processing pipeline with regard to identifying issues associated with the medical treatments for the medical condition of the patent and presenting a corresponding alerts or notifications in association with the representation in the GUI. For example, identifying one or more medical treatments that include a medication that the patient experienced an adverse reaction to, a medication that has caused unwanted side effects, a medication that has not helped control the patient's medical condition, or the like.

It should be appreciated that the mechanisms described in FIGS. 1-3 are only examples and are not intended to state or imply any limitation with regard to the type of cognitive system mechanisms with which the illustrative embodiments are implemented. Many modifications to the example cognitive system shown in FIGS. 1-3 may be implemented in various embodiments of the present invention without departing from the spirit and scope of the present invention.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment pathways, and other types of treatment pathway generation, e.g., items of interest to a particular user, potential new contact information, or the like.

IBM Watson™ is an example of one such cognitive system which can process human readable language and identify inferences between text passages with human-like high accuracy at speeds far faster than human beings and on a larger scale. In general, such cognitive systems are able to perform the following functions:

Navigate the complexities of human language and understanding,
Ingest and process vast amounts of structured and unstructured data,
Generate and evaluate hypothesis,
Weigh and evaluate responses that are based only on relevant evidence,
Provide situation-specific advice, insights, and guidance,
Improve knowledge and learn with each iteration and interaction through machine learning processes,
Enable decision making at the point of impact (contextual guidance),
Scale in proportion to the task,
Extend and magnify human expertise and cognition,
Identify resonating, human-like attributes and traits from natural language,
Deduce various language specific or agnostic attributes from natural language,
High degree of relevant recollection from data points (images, text, voice) (memorization and recall),
Predict and sense with situational awareness that mimic human cognition based on experiences, or
Answer questions based on natural language and specific evidence.

In one aspect, cognitive systems provide mechanisms for responding to requests posed to these cognitive systems using a request processing pipeline and/or process requests which may or may not be posed as natural language requests. The requests processing pipeline is an artificial intelligence application executing on data processing hardware that responds to requests pertaining to a given subject-matter domain presented in natural language. The request processing pipeline receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the request processing pipeline. The document may include any file, text, article, or source of data for use in the requests processing system. For example, a request processing pipeline accesses a body of knowledge about the domain, or subject matter area, e.g., financial domain, medical domain, legal domain, etc., where the body of knowledge (knowledgebase) can be organized in a variety of configurations, e.g., a structured repository of domain-specific information, such as ontologies, or unstructured data related to the domain, or a collection of natural language documents about the domain.

Content users input requests to cognitive system which implements the request processing pipeline. The request processing pipeline then responds to the requests using the content in the corpus of data by evaluating documents, sections of documents, portions of data in the corpus, or the like. When a process evaluates a given section of a document for semantic content, the process can use a variety of conventions to query such document from the request processing pipeline, e.g., sending the query to the request processing pipeline as a well-formed requests which is then interpreted by the request processing pipeline and a response is provided containing one or more responses to the request. Semantic content is content based on the relation between signifiers, such as words, phrases, signs, and symbols, and what they stand for, their denotation, or connotation. In other words, semantic content is content that interprets an expression, such as by using Natural Language Processing.

As will be described in greater detail hereafter, the request processing pipeline receives a request, parses the request to extract the major features of the request, uses the extracted features to formulate queries, and then applies those queries to the corpus of data. Based on the application of the queries to the corpus of data, the request processing pipeline generates a set of responses to the request, by looking across the corpus of data for portions of the corpus of data that have some potential for containing a valuable response to the request. The request processing pipeline then performs deep analysis on the language of the request and the language used in each of the portions of the corpus of data found during the application of the queries using a variety of reasoning algorithms. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the request and the found portions of the corpus of data. Other reasoning algorithms may look at temporal or spatial features in the language, while others may evaluate the source of the portion of the corpus of data and evaluate its veracity.

As mentioned above, request processing pipeline mechanisms operate by accessing information from a corpus of data or information (also referred to as a corpus of content), analyzing it, and then generating answer results based on the analysis of this data. Accessing information from a corpus of data typically includes: a database query that answers requests about what is in a collection of structured records, and a search that delivers a collection of document links in response to a query against a collection of unstructured data (text, markup language, etc.). Conventional request processing systems are capable of generating answers based on the corpus of data and the input request, verifying answers to a collection of request for the corpus of data, correcting errors in digital text using a corpus of data, and selecting responses to requests from a pool of potential answers, i.e. candidate answers.

FIG. 1 depicts a schematic diagram of one illustrative embodiment of a cognitive system 100 implementing a request processing pipeline 108, which in some embodiments may be a request processing pipeline, in a computer network 102. For purposes of the present description, it will be assumed that the request processing pipeline 108 that operates on structured and/or unstructured requests in the form of requests. One example of a question processing operation which may be used in conjunction with the principles described herein is described in U.S. Patent Application Publication No. 2011/0125734, which is herein incorporated by reference in its entirety. The cognitive system 100 is implemented on one or more computing devices 104A-D (comprising one or more processors and one or more memories, and potentially any other computing device elements generally known in the art including buses, storage devices, communication interfaces, and the like) connected to the computer network 102. For purposes of illustration only, FIG. 1 depicts the cognitive system 100 being implemented on computing device 104A only, but as noted above the cognitive system 100 may be distributed across multiple computing devices, such as a plurality of computing devices 104A-D. The network 102 includes multiple computing devices 104A-D, which may operate as server computing devices, and 110-112 which may operate as client computing devices, in communication with each other and with other devices or components via one or more wired and/or wireless data communication links, where each communication link comprises one or more of wires, routers, switches, transmitters, receivers, or the like. In some illustrative embodiments, the cognitive system 100 and network 102 enables request processing functionality for one or more cognitive system users via their respective computing devices 110-112. In other embodiments, the cognitive system 100 and network 102 may provide other types of cognitive operations including, but not limited to, request processing and cognitive response generation which may take many different forms depending upon the desired implementation, e.g., cognitive information retrieval, training/instruction of users, cognitive evaluation of data, or the like. Other embodiments of the cognitive system 100 may be used with components, systems, sub-systems, and/or devices other than those that are depicted herein.

The cognitive system 100 is configured to implement a request processing pipeline 108 that receive inputs from various sources. The requests may be posed in the form of natural language request for information, natural language request for the performance of a cognitive operation, or the like. For example, the cognitive system 100 receives input from the network 102, a corpus or corpora of electronic documents 140, cognitive system users, and/or other data and other possible sources of input. In one embodiment, some or all of the inputs to the cognitive system 100 are routed through the network 102. The various computing devices 104A-D on the network 102 include access points for content creators and cognitive system users. Some of the computing devices 104A-D include devices for a database storing the corpus or corpora of data 140 (which is shown as a separate entity in FIG. 1 for illustrative purposes only).

Portions of the corpus or corpora of data 140 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus or corpora of data 140 for use as part of a corpus of data with the cognitive system 100. The document includes any file, text, article, or source of data for use in the cognitive system 100. Cognitive system users access the cognitive system 100 via a network connection or an Internet connection to the network 102, and requests to the cognitive system 140 that are responded to/processed based on the content in the corpus or corpora of data 140. In one embodiment, the requests are formed using natural language. The cognitive system 100 parses and interprets the request via a pipeline 108, and provides a response to the cognitive system user, e.g., cognitive system user 110, containing one or more responses to the request posed, response to the request, results of processing the request, or the like. In some embodiments, the cognitive system 100 provides a response to users in a ranked list of candidate responses while in other illustrative embodiments, the cognitive system 100 provides a single final response or a combination of a final response and ranked listing of other candidate responses.

The cognitive system 100 implements the pipeline 108 which comprises a plurality of stages for processing a request based on information obtained from the corpus or corpora of data 140. The pipeline 108 generates responses for the request based on the processing of the request and the corpus or corpora of data 140. The pipeline 108 will be described in greater detail hereafter with regard to FIG. 3.

In some illustrative embodiments, the cognitive system 100 may be the IBM Watson™ cognitive system available from International Business Machines Corporation of Armonk, N.Y., which is augmented with the mechanisms of the illustrative embodiments described hereafter. As outlined previously, a pipeline of the IBM Watson™ cognitive system receives a request which it then parses to extract the major features of the request, which in turn are then used to formulate queries that are applied to the corpus or corpora of data 140. Based on the application of the queries to the corpus or corpora of data 140, a set of hypotheses, or responses to the request, are generated by looking across the corpus or corpora of data 140 for portions of the corpus or corpora of data 140 (hereafter referred to simply as the corpus 140) that have some potential for containing a valuable response to the response. The pipeline 108 of the IBM Watson™ cognitive system then performs deep analysis on the language of the request and the language used in each of the portions of the corpus 140 found during the application of the queries using a variety of reasoning algorithms.

The scores obtained from the various reasoning algorithms are then weighted against a statistical model that summarizes a level of confidence that the pipeline 108 of the IBM Watson™ cognitive system 100, in this example, has regarding the evidence that the potential candidate response is inferred by the request. This process is be repeated for each of the candidate responses to generate ranked listing of candidate responses which may then be presented to the user that submitted the request, e.g., a user of client computing device 110, or from which a final response is selected and presented to the user. More information about the pipeline 108 of the IBM Watson™ cognitive system 100 may be obtained, for example, from the IBM Corporation website, IBM Redbooks, and the like. For example, information about the pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 100 from a client device may be posed in the form of a natural language request, the illustrative embodiments are not limited to such. Rather, the request may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing patient medical records, medical guidance documentation from one or more corpora, and the like, to provide a healthcare oriented cognitive system result.

In the context of the present invention, cognitive system 100 may provide a cognitive functionality for presenting contextually relevant patient data in relation to other patients to a medical professional in a graphical user interface. For example, depending upon the particular implementation, the healthcare based operations may comprise patient diagnostics, precision cohort systems, medical practice management systems, personal patient care plan generation and monitoring, patient electronic medical record (EMR) evaluation for various purposes, such as for identifying patients that are suitable for a medical trial or a particular type of medical treatment, or the like. Thus, the cognitive system 100 may be a cognitive system 100 that operates in the medical or healthcare type domains and which may process requests for such healthcare operations via the request processing pipeline 108 input as either structured requests, unstructured requests, or the like. In one illustrative embodiment, the cognitive system 100 is a cognitive precision cohort system 100 that analyzes a patient's EMR in relation to medical guidelines and other medical documentation in a corpus of information to generate treatment pathway information with regard to a medical malady or condition of the patient.

As shown in FIG. 1, the cognitive system 100 is further augmented, in accordance with the mechanisms of the illustrative embodiments, to include logic implemented in specialized hardware, software executed on hardware, or any combination of specialized hardware and software executed on hardware, for implementing a cognitive system 120 that generates a graphical user interface (GUI) configured to present the most relevant information for treating a patient in relation to other patients based on a context of the patient being treated. As shown in FIG. 1, cognitive precision cohort system 120 comprises medical condition identification engine 122, medical treatment identification engine 124, curation engine 126, and presentation engine 128.

In the initialization of cognitive system 100 and, more specifically, cognitive precision cohort system 120, medical condition identification engine 122 analyzes electronic medical records (EMR) of a patient stored in corpus or corpora of data 140 to identify a medical condition associated with the patient. As stated previously, corpus or corpora of data 140 may include one corpus for medical treatment guideline documents and another corpus for electronic medical record documents. Thus, in addition to medical condition identification engine 122 analyzing the electronic medical records (EMR) of the patient stored in corpus or corpora of data 140 in order to identify a medical condition associated with the patient, medical treatment identification engine 124 identifies a set of treatments for the patient's medical condition from a set of medical treatment guidelines stored in corpus or corpora of data 140. In order to identify how the treatments for the medical condition have worked for other patients with the same medical condition, medical condition identification engine 122 identifies a cohort of similar patients with a same medical condition as the patient's medical condition. Utilizing the patient's medical condition and the set of treatments for the patient's medical condition, curation engine 126 identifies a current treatment that the patient is following.

Curation engine 126 then identifies a cohort of other patients that have followed the treatment currently being followed by the patient. For those patients in the cohort of patients that have followed the treatment currently being followed by the patient, curation engine 126 identifies a set of next treatments that those patients followed, i.e. a treatment immediately following the treatment currently being followed by the patient which the patients also followed. Curation engine 126 identifies which of those next treatments improved the medical condition of patients within the cohort of similar patients with the same medical condition as well as which of those next treatments failed to improve the medical condition of patients within the cohort of other patients with the same medical condition. That is, curation engine 126 identifies whether the specific next treatment controlled or failed to control the medical condition based on whether the medical condition improved following the requirements of the treatments utilizing lab results of each of the other patients, less symptoms indicated by each of the other patients, or the like. Therefore, curation engine 126 utilizes the outcomes of the other patients to identify whether the next treatment improved the medical condition, whether the treatment worsened the medical condition, or whether the treatment had no statistical difference on the medical condition. Utilizing these determinations, curation engine 126 provides an indication of the set of next treatments the cohort of similar patients were prescribed, a number of patients in the cohort of similar patients following each treatment in the set of next treatments, an indication as to whether each treatment in the set of next treatments controlled or failed to control the same medical condition for the cohort of similar patients, and a statistical significance comparing a number or percent controlled of the cohort of similar patients in each next treatment to patients in the cohort of similar patients staying on the current treatment. Curation engine 126 may provide the identification using statistical number identified across the entire patient population having the same medical condition as that of the patient.

However, curation engine 126 may also curate the patient population having the same medical condition based on a set of characteristics thereby forming a patient cohort. That is, curation engine 126 may limit the number of other patients to consider based on a set of characteristics that the patient has in common with the other patients other than having the same medical condition. That is, if the patient has, for example, preexisting vices of smoking or alcohol use, then curation engine 126 may select patients from the other patients with the same medical condition that also have preexisting vices of smoking or alcohol use. As another example, if the patient utilizes certain medications for another medical condition, then curation engine 126 may select patients from the other patients that also use those medications. As yet other examples, curation engine 126 may limit the number of other patients with the same medical condition to consider based on lab results, immunizations, other similar or the same medical conditions, or the like. In accordance with the illustrative embodiments, the characteristics that are used to limit the number of other patients to consider may be predetermined or may be selected by the medical professional treating the patient.

Once the determinations and indications have been provided by curation engine 126, presentation engine 128 presents the set of treatments other patients have followed for the patient's medical condition to a medical professional in a graphical user interface (GUI). The presentation may identify one or more of:

a set of next treatments the cohort of similar patients were prescribed, a number of patients in the cohort of similar patients following each treatment in the set of next treatments, an indication as to whether each treatment in the set of next treatments controlled or failed to control the same medical condition for the cohort of similar patients, a statistical significance comparing a number or percent controlled of the cohort of similar patients in each next treatment to patients in the cohort of similar patients staying on the current treatment, or reasons for discontinuing the current treatment.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 2 is provided as an example of one type of data processing system in which aspects of the present invention may be implemented. Many other types of data processing systems may be likewise configured to specifically implement the mechanisms of the illustrative embodiments.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which, which implements a cognitive system 100 and QA system pipeline 108 augmented to include the additional mechanisms of the illustrative embodiments described hereafter.

In the depicted example, data processing system 200 employs a hub architecture including north bridge and memory controller hub (NB/MCH) 202 and south bridge and input/output (I/O) controller hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 8®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System P® computer system, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 is an example diagram illustrating an interaction of elements of a cognitive system in accordance with one illustrative embodiment. The example diagram of FIG. 3 depicts an implementation of a cognitive system 300, which may be a cognitive system such as cognitive system 100 described in FIG. 1, that is configured to present contextually relevant patient data in relation to other patients to a medical professional in a graphical user interface. However, it should be appreciated that this is only an example implementation and other healthcare operations may be implemented in other embodiments of the healthcare cognitive system 300 without departing from the spirit and scope of the present invention.

Moreover, it should be appreciated that while FIG. 3 depicts patient 302 and medical professional 306 as human figures, the interactions with and between these entities may be performed using computing devices, medical equipment, and/or the like, such that entities 302 and 306 may in fact be computing devices, e.g., client computing devices. For example, interactions 304, 314, 316, and 330 between patient 302 and user 306 may be performed orally, e.g., a doctor interviewing a patient, and may involve the use of one or more medical instruments, monitoring devices, or the like, to collect information that may be input to the cognitive system 300 as patient attributes 318. Interactions between user 306 and cognitive system 300 will be electronic via a user computing device (not shown), such as a client computing device 110 or 112 in FIG. 1, communicating with cognitive system 300 via one or more data communication links and potentially one or more data networks.

As shown in FIG. 3, in accordance with one illustrative embodiment, a patient 302 presents symptoms 304 of a medical malady or condition to a user 306, such as a medical professional, healthcare practitioner, technician, or the like. User 306 may interact with patient 302 via a question 314 and response 316 exchange where user 306 gathers more information about patient 302, symptoms 304, and the medical malady or condition of patient 302. It should be appreciated that the questions/responses may in fact also represent user 306 gathering information from patient 302 using various medical equipment, e.g., blood pressure monitors, thermometers, wearable health and activity monitoring devices associated with patient 302 such as a FitBit™, a wearable heart monitor, or any other medical equipment that may monitor one or more medical characteristics of patient 302. In some cases such medical equipment may be medical equipment typically used in hospitals or medical centers to monitor vital signs and medical conditions of patients that are present in hospital beds for observation or medical treatment.

In response, user 306 submits request 308 to cognitive system 300, such as via a user interface on a client computing device that is configured to allow users to submit requests to cognitive system 300 in a format that cognitive system 300 is able to parse and process. Request 308 may include, or be accompanied with, information identifying patient attributes 318. These patient attributes 318 may include, for example, an identifier of patient 302 from which patient EMRs 322 for patient 302 may be retrieved, demographic information about patient 302, symptoms 304, and other pertinent information obtained from responses 316 to questions 314 or information obtained from medical equipment used to monitor or gather data about the condition of patient 302, including a medical conditions associated with patient 302. Any information about patient 302 that may be relevant to a cognitive evaluation of patient 302 by cognitive system 300 may be included in request 308 and/or patient attributes 318.

Cognitive system 300 is specifically configured to perform an implementation specific healthcare oriented cognitive operation. In the depicted example, this cognitive precision cohort operation is directed to providing a set of treatment pathways 328 associated with the medical condition of patient 302 to user 306 to assist user 306 in treating patient 302 based on their reported symptoms 304 and other information gathered about patient 302 via question 314 and response 316 process and/or medical equipment monitoring/data gathering. Cognitive system 300 operates on request 308 and patient attributes 318 utilizing information gathered from medical corpus and other source data 326, treatment pathways data 324, and patient EMRs 322 associated with the patient 302 to generate one or more treatment pathways 328 that a similar cohort of patients have followed. Treatment pathways 328 may be presented with associated supporting evidence, obtained from the patient attributes 318 and data sources 322, 324, and 326, indicating the reasoning as to why the treatment pathways 328 is being provided.

For example, based on request 308 and patient attributes 318, cognitive system 300 may operate on the request to parse request 308 and patient attributes 318 to determine what is being requested and the criteria upon which the request is to be generated as identified by patient attributes 318, and may perform various operations for generating queries that are sent to the data sources 322, 324, and 326 to retrieve data, generate associated indications associated with the data, and provides supporting evidence found in the data sources 322, 324, and 326. In the depicted example, patient EMRs 322 is a patient information repository that collects patient data from a variety of sources, e.g., hospitals, laboratories, physicians' offices, health insurance companies, pharmacies, etc. Patient EMRs 322 store various information about individual patients, such as patient 302, in a manner (structured, unstructured, or a mix of structured and unstructured formats) that the information may be retrieved and processed by cognitive system 300. This patient information may comprise various demographic information about patients, personal contact information about patients, employment information, health insurance information, laboratory reports, physician reports from office visits, hospital charts, historical information regarding previous diagnoses, symptoms, treatments, prescription information, etc. Based on an identifier of the patient 302, the patient's corresponding EMRs 322 from this patient repository may be retrieved by cognitive system 300 and searched/processed to provide treatment pathways 328 that a similar cohort of patients have followed.

Treatment pathways data 324 provides a knowledge base of medical knowledge that is used to identify potential treatments for a patient's medical condition based on patient's attributes 318 and historical information presented in patient's EMRs 322. Treatment pathways data 324 may be obtained from official treatment guidelines and policies issued by medical authorities, e.g., the American Medical Association, may be obtained from widely accepted physician medical and reference texts, e.g., the Physician's Desk Reference, insurance company guidelines, or the like. The treatment pathways data 324 may be provided in any suitable form that may be ingested by the cognitive system 300 including both structured and unstructured formats.

In some cases, such treatment pathways data 324 may be provided in the form of rules that indicate the criteria required to be present, and/or required not to be present, for the corresponding treatment to be applicable to a particular patient for treating a particular symptom or medical malady/condition. For example, the treatment pathways data 324 may comprise a treatment pathways rule that indicates that for a treatment of Decitabine, strict criteria for the use of such a treatment is that patient 302 is less than or equal to 60 years of age, has acute myeloid leukemia (AML), and no evidence of cardiac disease. Thus, for a patient 302 that is 59 years of age, has AML, and does not have any evidence in their patient attributes 318 or patient EMRs 322 indicating evidence of cardiac disease, the following conditions of the treatment rule exist:

Age<=60 years=59(MET);

Patient has AML=AML(MET); and

Cardiac Disease=false(MET)

Since all of the criteria of the treatment rule are met by the specific information about this patient 302, then the treatment of Decitabine is a candidate treatment pathway for consideration for this patient 302. However, if the patient had been 69 years old, the first criterion would not have been met and the Decitabine treatment would not be a candidate treatment pathway for consideration for this patient 302. Various potential treatment pathways may be evaluated by cognitive system 300 based on ingested treatment pathways data 324 to identify subsets of candidate treatment pathways for further consideration by cognitive system 300 by identifying such candidate treatment pathways based on evidential data obtained from patient EMRs 322 and medical corpus and other source data 326.

For example, data mining processes may be employed to mine the data in sources 322 and 326 to identify evidential data supporting and/or refuting the applicability of the candidate treatment pathways to the particular patient 302 as characterized by the patient's patient attributes 318 and EMRs 322. For example, for each of the criteria of the treatment rule, the results of the data mining provides a set of evidence that supports giving the treatment in the cases where the criterion is "MET" and in cases where the criterion is "NOT MET." Cognitive system 300 processes the evidence in accordance with various cognitive logic algorithms to generate an indicator for each candidate treatment pathways indicating a confidence that the corresponding candidate treatment pathways are valid for patient 302. The candidate treatment pathways may then be presented to user 306 as a listing of treatment pathways 328. Treatment pathways 328 may be presented to user 306 in a manner that the underlying evidence evaluated by cognitive system 300 may be accessible, such as via a drilldown interface, so that user 306 may identify the reasons why treatment pathways 328 is being provided by cognitive system 300.

In accordance with the illustrative embodiments herein, cognitive system 300 is augmented to include cognitive precision cohort system 340. Cognitive precision cohort system 340 comprises medical condition identification engine 342, medical treatment identification engine 344, curation engine 346, and presentation engine 348 which operate in a similar manner as previously described above with regard to corresponding elements 122-128 in FIG. 1. That is, medical condition identification engine 342 initially analyzes electronic medical records (EMR) of patient 302 stored in patient EMR corpus 322 to identify a medical condition associated with patient 302. Medical treatment identification engine 344 then identifies a set of treatments for the patient's medical condition from a set of medical treatment guidelines stored in treatment pathways data 324 and/or medical corpus and other source data 326. In order to identify how the treatments for the medical condition have worked for other patients with the same medical condition, medical condition identification engine 342 further identifies other patients with a same medical condition as the patient's medical condition. Utilizing the patient's medical condition and the set of treatments for the patient's medical condition identified, curation engine 346 identifies a current treatment that patient 302 is following.

Additionally, curation engine 346 identifies a cohort of other patients that have followed the treatment currently being followed by the patient. For those patients in the cohort of patients that have followed the treatment currently being followed by the patient, curation engine 346 identifies a set of next treatments that those patients followed, i.e. a treatment immediately following the treatment currently being followed by the patient which the patients also followed. Curation engine 346 identifies which of those next treatments improved the medical condition of patients within the cohort of similar patients with the same medical condition as well as which of those next treatments failed to improve the medical condition of patients within the cohort of other patients with the same medical condition. That is, performing similar operations to those performed above for the patient, curation engine 346 whether the specific next treatment controlled or failed to control the medical condition based on whether the medical condition improved following the requirements of the treatments utilizing lab results of each of the other patients, less symptoms indicated by each of the other patients, or the like. Therefore, curation engine 346 utilizes the outcomes of the other patients to identify whether the next treatment improved the medical condition, whether the treatment worsened the medical condition, or whether the treatment had no statistical difference on the medical condition. Utilizing these determinations, curation engine 346 provides an indication of the set of next treatments the cohort of similar patients were prescribed, a number of patients in the cohort of similar patients following each treatment in the set of next treatments, an indication as to whether each treatment in the set of next treatments controlled or failed to control the same medical condition for the cohort of similar patients, and a statistical significance comparing a number or percent controlled of the cohort of similar patients in each next treatment to patients in the cohort of similar patients staying on the current treatment. Curation engine 346 may provide the identification using statistical number identified across the entire patient population having the same medical condition as that of the patient.

However, curation engine 346 may also curate the patient population having the same medical condition based on a set of characteristics thereby forming a patient cohort. That is, curation engine 346 may limit the number of other patients to consider based on a set of characteristics that the patient has in common with the other patients other than having the same medical condition. That is, if the patient has, for example, preexisting vices of smoking or alcohol use, then curation engine 346 may select patients from the other patients with the same medical condition that also have preexisting vices of smoking or alcohol use. As another example, if the patient utilizes certain medications for another medical condition, then curation engine 346 may select patients from the other patients that also use those medications. As yet other examples, curation engine 346 may limit the number of other patients with the same medical condition to consider based on lab results, immunizations, other similar or the same medical conditions, or the like. In accordance with the illustrative embodiments, the characteristics that are used to limit the number of other patients to consider may be predetermined or may be selected by the medical professional treating the patient.

Once the determinations and indications have been provided by curation engine 346, presentation engine 348 presents the set of treatments other patients have followed for the patient's medical condition to a medical professional in a graphical user interface (GUI). The presentation may identify one or more of:
 a set of next treatments the cohort of similar patients were prescribed,
 a number of patients in the cohort of similar patients following each treatment in the set of next treatments,
 an indication as to whether each treatment in the set of next treatments controlled or failed to control the same medical condition for the cohort of similar patients,
 a statistical significance comparing a number or percent controlled of the cohort of similar patients in each next treatment to patients in the cohort of similar patients staying on the current treatment, or
 reasons for discontinuing the current treatment.

Thus, the illustrative embodiments provide mechanisms for presenting contextually relevant patient data in relation to other patients to a medical professional in a graphical user interface. The cognitive precision cohort system generates a graphical user interface (GUI) that is configured to present the most relevant information for treating a patient based on a context of the patient being treated. The cognitive precision cohort system provides a historical data representation in the GUI of patients that follow each treatment path for a medical condition. The cognitive precision cohort system also provides information about how many of those patients have their medical condition under control as well as those patients that do not have their medical condition under control. Each row of information presented in the GUI indicates separate treatments, as determined from medical treatment guidelines, with blocks within each row being representative of different medications included in that treatment.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Figure 4:
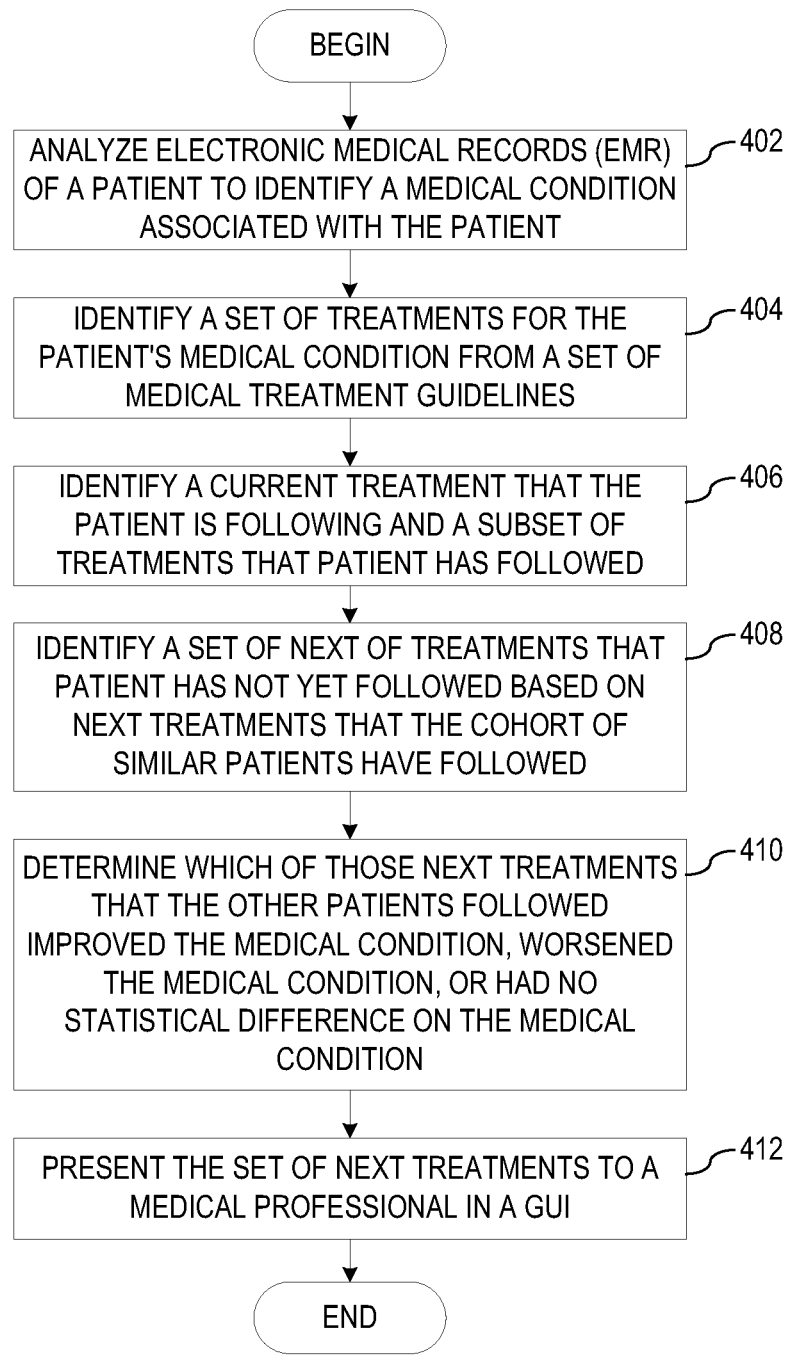
FIG. 4 depicts an exemplary flowchart of the operation performed by a cognitive precision cohort system in presenting contextually relevant patient data in relation to other patients to a medical professional in a graphical user interface in accordance with an illustrative embodiment.

FIG. 4 depicts an exemplary flowchart of the operation performed by a cognitive precision cohort system in presenting contextually relevant patient data in relation to other patients to a medical professional in a graphical user interface in accordance with an illustrative embodiment. As the operation begins, the cognitive precision cohort system analyzes electronic medical records (EMR) of a patient to identify a medical condition associated with the patient (step 402). The cognitive precision cohort system then identifies a set of treatments for the patient's medical condition from a set of medical treatment guidelines (step 404). With the patient's medical condition and the set of treatments for the patient's medical condition identified, the cognitive precision cohort system identifies a current treatment that the patient is following and a subset of treatments that patient has followed (step 406). With the patient's medical condition and the set of treatments for the patient's medical condition identified, the cognitive precision cohort system identifies a set of next treatments that other patient have followed after following the current treatment that the patient is following and each of the cohort of similar patients are following or have followed (step 408). For each next treatment, the cognitive precision cohort system determines whether the next treatment that the other patients followed improved the medical condition, determines which of those treatments that the other patients followed worsened the medical condition, or determines which of those treatments that the other patients followed had no statistical difference on the medical condition (step 410). The cognitive precision cohort system presents the set of treatments that the patient has yet to follow to a medical professional in a graphical user interface (GUI) (step 412) with an identification of one or more of:

a set of next treatments the cohort of similar patients were prescribed, a number of patients in the cohort of similar patients following each treatment in the set of next treatments, an indication as to whether each treatment in the set of next treatments controlled or failed to control the same medical condition for the cohort of similar patients, a statistical significance comparing a number or percent controlled of the cohort of similar patients in each next treatment to patients in the cohort of similar patients staying on the current treatment, or reasons for discontinuing the current treatment.

After presenting the set of treatments that the patient has yet to follow to the medical professional in the graphical user interface, the operation terminates.

The cognitive precision cohort system may rank the treatments that the other patients have followed based on the outcomes of the cohort of similar patients. The cognitive precision cohort system may curate the other patients having the same medical condition based on a set of characteristics thereby forming a patient cohort. That is, the cognitive precision cohort system may limit the number of other patients to consider based on a set of characteristics that the patient has in common with the other patients other than having the same medical condition.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Thus, the illustrative embodiments provide mechanisms for presenting contextually relevant patient data to a medical professional in a graphical user interface. The cognitive precision cohort system generates a graphical user interface (GUI) that is configured to present the most relevant information for treating a patient based on a context of the patient being treated. The cognitive precision cohort system provides a historical data representation in the GUI of patients that follow each treatment path for a medical condition. The cognitive precision cohort system also provides information about how many of those patients have their medical condition under control as well as those patients that do not have their medical condition under control. Each row of information presented in the GUI indicates separate treatments, as determined from medical treatment guidelines, with blocks within each row being representative of different medications included in that treatment.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, the at least one memory comprising instructions executed by the at least one processor to cause the at least one processor to implement a cognitive precision cohort system, wherein the cognitive precision cohort system operates to:

analyzing, by the cognitive precision cohort system, electronic medical records (EMRs) of a patient to identify a medical condition associated with the patient;

identifying, by the cognitive precision cohort system, a set of treatments from a corpus of medical treatment guidelines for the patient's medical condition;

identifying, by the cognitive precision cohort system, a current treatment that the patient is following;

identifying, by the cognitive precision cohort system, a first cohort of similar patients with the same medical condition as the patient's medical condition following the current treatment and a second cohort of similar patients with the same medical condition as the patient's medical condition that have followed the current treatment but are no longer following the current treatment;

for those patients in the second cohort of similar patients, identifying, by the cognitive precision cohort system, a set of next treatments from the set of treatments that each patient of the second cohort of similar patients followed;

for each next treatment followed by a patient in the second cohort of similar patients, determining, by the cognitive precision cohort system, whether the next treatment controlled or failed to control the same medical condition for the patient;

presenting, by the cognitive precision cohort system in a graphical user interface, the set of next treatments the second cohort of similar patients were prescribed, a number of patients in the second cohort of similar patients following each next treatment in the set of next treatments, an indication as to whether each next treatment in the set of next treatments controlled or failed to control the same medical condition for the second cohort of similar patients, and a statistical significance comparing a number controlled of patients in the second cohort of similar patients following each next treatment to patients in the first cohort of similar patients following the current treatment;

for each treatment in the set of treatments that the second cohort of similar patients followed, determining, by the cognitive precision cohort system, whether the treatment in the set of treatments that each other patient in the second cohort of similar patients followed controlled or failed to control the other patient's medical condition;

identifying, by the cognitive precision cohort system, effects of the treatment and reasons for discontinuing the treatment;

presenting, by the cognitive precision cohort system in the graphical user interface, treatments in the set of treatments that the other patients followed that controlled the other patient's medical condition and effects of the treatment and reasons for discontinuing the treatment captured from the other patient's structured and unstructured data in the electronic medical record (EMR); and presenting, by the cognitive precision cohort system in the graphical user interface, treatments in the set of treatments that the other patients have followed that failed to control the other patient's medical condition and effects of the treatment and reasons for discontinuing the treatment captured from the other patient's structured and unstructured data in the electronic medical record (EMR).

2. The method of claim 1, wherein the next treatments in the set of next treatments that the second cohort of similar patients followed are ranked according to a percent controlled of that next treatment.

3. The method of claim 1, wherein the first cohort of similar patients with the same medical condition and the second cohort of similar patients are curated to include only patients with the same medical condition and that have a set of characteristics in common with the patient other than having the same medical condition.

4. A computer program product comprising a computer readable storage medium having a computer readable program stored therein, wherein the computer readable program, when executed on a computing device, causes the computing device to:

analyze electronic medical records (EMRs) of a patient to identify a medical condition associated with the patient;

identify a set of treatments from a corpus of medical treatment guidelines for the patient's medical condition;

identify a current treatment that the patient is following;

identify a first cohort of similar patients with the same medical condition as the patient's medical condition following the current treatment and a second cohort of similar patients with the same medical condition as the patient's medical condition that have followed the current treatment but are no longer following the current treatment;

for those patients in the second cohort of similar patients, identify a set of next treatments from the set of treatments that each patient of the second cohort of similar patients followed;

for each next treatment followed by a patient in the second cohort of similar patients, determine whether the next treatment controlled or failed to control the same medical condition for the patient; and present, in a graphical user interface, the set of next treatments the second cohort of similar patients were prescribed, a number of patients in the second cohort of similar patients following each next treatment in the set of next treatments, an indication as to whether each next treatment in the set of next treatments controlled or failed to control the same medical condition for the second cohort of similar patients, and a statistical significance comparing a number controlled of patients in the second cohort of similar patients following each next treatment to patients in the first cohort of similar patients following the current treatment;

for each treatment in the set of treatments that the second cohort of similar patients followed, determine whether the treatment in the set of treatments that each other patient in the second cohort of similar patients followed controlled or failed to control the other patient's medical condition;

identify effects of the treatment and reasons for discontinuing the treatment;

present treatments in the set of treatments that the other patients followed that controlled the other patient's medical condition and effects of the treatment and reasons for discontinuing the treatment captured from the other patient's structured and unstructured data in the electronic medical record (EMR); and present treatments in the set of treatments that the other patients have followed that failed to control the other patient's medical condition and effects of the treatment and reasons for discontinuing the treatment captured from the other patient's structured and unstructured data in the electronic medical record (EMR).

5. The computer program product of claim 4, wherein the next treatments in the set of next treatments that the second cohort of similar patients followed are ranked according to a percent controlled of that next treatment.

6. The computer program product of claim 4, wherein the first cohort of similar patients with the same medical condition and the second cohort of similar patients are curated to include only patients with the same medical condition and that have a set of characteristics in common with the patient other than having the same medical condition.

7. An apparatus comprising:
a processor; and
a memory coupled to the processor, wherein the memory comprises instructions which, when executed by the processor, cause the processor to:

analyze electronic medical records (EMRs) of a patient to identify a medical condition associated with the patient;

identify a set of treatments from a corpus of medical treatment guidelines for the patient's medical condition;

identify a current treatment that the patient is following;

identity a first cohort of similar patients with the same medical condition as the patient's medical condition following the current treatment and a second cohort of similar patients with the same medical condition as the patient's medical condition that have followed the current treatment but are no longer following the current treatment;

for those patients in the second cohort of similar patients, identify a set of next treatments from the set of treatments that each patient of the second cohort of similar patients followed;

for each next treatment followed by a patient in the second cohort of similar patients, determine whether the next treatment controlled or failed to control the same medical condition for the patient; and present, in a graphical user interface, the set of next treatments the second cohort of similar patients were prescribed, a number of patients in the second cohort of similar patients following each next treatment in the set of next treatments, an indication as to whether each next treatment in the set of next treatments controlled or failed to control the same medical condition for the second cohort of similar patients, and a statistical significance comparing a number controlled of patients in the second cohort of similar patients following each next treatment, to patients in the first cohort of similar patients following the current treatment;

for each treatment in the set of treatments that the second cohort of similar patients followed, determine whether the treatment in the set of treatments that each other patient in the second cohort of similar patients followed controlled or failed to control the other patient's medical condition;

identify effects of the treatment and reasons for discontinuing the treatment;

present treatments in the set of treatments that the other patients followed that controlled the other patient's medical condition and effects of the treatment and reasons for discontinuing the treatment captured from the other patient's structured and unstructured data in the electronic medical record (EMR); and present treatments in the set of treatments that the other patients have followed that failed to control the other patient's medical condition and effects of the treatment and reasons for discontinuing the treatment captured from the other patient's structured and unstructured data in the electronic medical record (EMR).

8. The apparatus of claim 7, wherein the next treatments in the set of next treatments that the second cohort of similar patients followed are ranked according to a percent controlled of that next treatment.

9. The apparatus of claim 7, wherein the first cohort of similar patients with the same medical condition and the second cohort of similar patients are curated to include only patients with the same medical condition and that have a set of characteristics in common with the patient other than having the same medical condition.

* * * * *